United States Patent [19]
Orr et al.

[11] Patent Number: 5,394,877
[45] Date of Patent: Mar. 7, 1995

[54] ULTRASOUND MEDICAL DIAGNOSTIC DEVICE HAVING A COUPLING MEDIUM PROVIDING SELF-ADHERENCE TO A PATIENT

[75] Inventors: Joseph A. Orr; Dwayne R. Westenskow, both of Salt Lake City; Fidel H. Silva, Sandy, all of Utah

[73] Assignee: Axon Medical, Inc., Salt Lake City, Utah

[21] Appl. No.: 216,079

[22] Filed: Mar. 21, 1994

Related U.S. Application Data

[63] Continuation of Ser. No. 45,916, Apr., 1993, abandoned.

[51] Int. Cl.6 .............................................. A61B 8/00
[52] U.S. Cl. ................................ 128/662.03; 128/640
[58] Field of Search .................... 128/662.03, 639, 640, 128/643, 798, 802, 803, 891; 607/149, 150

[56] References Cited

U.S. PATENT DOCUMENTS

| | | | |
|---|---|---|---|
| 4,122,837 | 10/1978 | Leonard | 128/774 |
| 4,391,278 | 7/1983 | Cahalan et al. | 128/640 |
| 4,458,696 | 7/1984 | Larimore | 128/798 |
| 4,556,066 | 12/1985 | Semrow | 128/662.03 |
| 4,593,053 | 6/1986 | Jevne et al. | 523/111 |
| 4,947,853 | 8/1990 | Hon | 128/662.03 |
| 5,020,547 | 6/1991 | Strock | 128/891 |
| 5,058,592 | 10/1991 | Whisler | 128/662.03 |
| 5,070,888 | 12/1991 | Hon et al. | 128/778 |
| 5,131,401 | 7/1992 | Westenskow et al. | 128/741 |
| 5,168,876 | 12/1992 | Quedens et al. | 128/642 |
| 5,168,879 | 12/1992 | Dukes et al. | 128/775 |
| 5,212,988 | 5/1993 | White et al. | 73/599 |
| 5,213,104 | 5/1993 | Reynolds | 128/661.07 |
| 5,215,094 | 6/1993 | Franklin et al. | 128/661.08 |

OTHER PUBLICATIONS

Brochure from Gorometrics Medical Systems, Inc. entitled–"Tired of All the Belt Tightening", undated.
Brochure from Promeon ® Hydrogels, Nov. 1989.
Freeman, Roger K., et al. "Instrumentation, Artifact Detection, and Fetal Arrhythmias", *Fetal Heart Rate Monitoring*, Williams & Wilkins, Baltimore, undated, pp. 28–54.
Graseby Medical Respiration Sensor label, undated.
Gravenstein, J. S., et al., J. S., et al, "Monitoring Practice in Clinical Anesthesia", J. B. Lippincott Company, Philadelphia, undated, pp. 271-273.
Patrick, John, et al. "Analysis of Fetal Activity and Maternal and Fetal Heart Rate Using a Laboratory Minicomputer", *American Journal of Perinatology*, vol. 3, No. 2, Apr. 1986, pp. 123–126.
Randall, N. J., et al. "Detection of the fetal ECG during labour by an intrauterine probe", *J. Biomed Eng,* Apr. 1988, vol. 10, pp. 159–164.
Schwoobel, Eliane, et al, "Combined electronic fetal heart rate and fetal movement monitor – a preliminary report", *J. Perinat Med,* 1987, pp. 179-184.

*Primary Examiner*—George Manuel
*Attorney, Agent, or Firm*—Trask, Britt & Rossa

[57] ABSTRACT

A contact medium structure attachable to externally-applied medical diagnostic devices for providing self-adherence of the medical device to the skin of a patient thereby eliminating the need for belts or similar means. The contact medium is inherently adhesive, hydrophilic, skin-compatible, ultrasonic-compatible and pressure sensitive to facilitate self-adhesion of the medical device to the patient's skin. A particularly suitable contact medium is a mesh-reinforced hydrogel film which adheres to the device and extends beyond the perimeter of the device to provide additional adhesiveness and compliance with the contour of the patient's body. A support element associated with and extending beyond the perimeter of the medical device adheres to the contact medium and provides adjustability of the extended hydrogel film relative to the patient's skin.

28 Claims, 2 Drawing Sheets

ULTRASOUND MEDICAL DIAGNOSTIC DEVICE HAVING A COUPLING MEDIUM PROVIDING SELF-ADHERENCE TO A PATIENT

This application is a continuation of application Ser. No. 08/045,916, filed Apr. 12, 1993, now abandoned.

BACKGROUND

1. Field of the Invention

This invention relates to medical diagnostic devices and procedures which monitor or evaluate conditions within a body by means of externally positioned apparatus. Specifically, this invention relates to devices which are structured to provide self-adherence of a diagnostic device to a patient's skin through employment of a coupling medium having adherent properties in relation to the skin of the patient.

2. Statement of the Art

Many medical diagnostic devices are used externally to a patient's body to evaluate or monitor conditions which exist within the patient's body. A common example of such devices are ultrasound apparatus. Ultrasound refers to sound waves the frequencies of which are above those perceptible by the human ear. Because body tissues are generally good conductors of ultrasound, diagnostic methods using ultrasound are often used in medicine. In particular, sound waves with frequencies above one Megahertz (1 Mhz.) can be used to probe internal structures in the human body. During ultrasonic monitoring, high frequency sound waves are transmitted through the body from a source external to the body. By measuring the time and amplitude of sound waves reflected back to an ultrasonic sensor, one can measure tissue density and tissue movement. In most monitors, the ultrasonic transmitter and receiver are combined into a single transducer.

Ultrasound is used medically for imaging, fetal heart rate monitoring, air embolism detection and arterial mapping, and other applications. Of these applications, all but imaging are based on the Doppler effect. The Doppler effect is a detectable shift in frequency of the waves emanating from a moving object and can be used to determine the relative movement of that object. In fetal heart rate monitoring, for example, the Doppler shift principle is applied to detect shifts in frequency of ultrasound waves reflected from the moving valves of the fetal heart to determine fetal heart rate (FHR). In other medical monitoring applications, the Doppler shift occurs when ultrasound waves are reflected from moving blood cells in an artery or in the heart.

Specifically with respect to non-invasive FHR monitoring, an ultrasound device, including a transmitter and receiver, is positioned against the mother's abdomen and ultrasound waves are emitted into the body in the area of the fetus. The signal is continuously transmitted and reflected signals are continuously received. If the reflecting surface is not in motion, the frequency of the two signals remains the same. However, when the transmitted signal is reflected off a moving surface, such as the fetal heart, a frequency shift occurs. The detected frequency shift is converted to an electronic signal and is amplified so that the shift may be heard or visualized, or both.

Certain problems are encountered in ultrasound FHR monitoring one of the most significant being that the ultrasound often detects movement of maternal blood vessels in the area of the uterus and the signals can be confusing. It is necessary therefore, to move the ultrasound device around the area of the patient's abdomen until a strong signal is detected from the fetal heart. If the mother or fetus moves, the signal may be lost and the ultrasound device may have to be shifted again to obtain the best signal.

Once a strong signal is detected, the ultrasound device must be held in place during the monitoring session. That is accomplished either by holding the device in place by hand or by strapping the device to the patient by means of a belt encircling the body of the patient. Since monitoring sessions can last an hour or longer, holding the ultrasound device by hand can be uncomfortable and inconvenient. However, strapping the device to the patient may be uncomfortable for the patient and requires occasional adjustment.

The problems of strapping external medical devices to a patient's abdomen has been addressed in U.S. Pat. No. 5,070,888 to Hon, et al., issued Dec. 10, 1991 in which is disclosed a tocodynamometer having a concave support base for application to the patient's abdomen. The Hon device employs a sheet of adhesive material covering the support base and requires the application of an adhesive binder solution to the abdomen of the patient to effect bonding. The Hon device does not accommodate the continuous movement of the device about the patient's abdomen.

A second concern in conducting ultrasound diagnosis is the problem associated with the coupling medium used to contact the ultrasound device with the patient's skin. That is, it is necessary in performing an ultrasound procedure to have proper acoustical coupling between the ultrasound transducer and the patient's skin to facilitate transmission of the sound wave through the skin and other body tissues. If, for example, air pockets form between the ultrasound transducer and the patient's skin, the sound wave is merely deflected back to the transducer without passing into the body because air is less dense than tissue. Therefore, it is important to provide a coupling medium between the transducer and the patient's skin which is acoustically compatible, or which has a density similar to body tissue, in order to optimize transmission of the sound waves.

In prior art devices and procedures, a fluid-like transmission gel is applied to the patient's skin in the area of treatment, and the ultrasound transducer is moved over the gel and over the patient's skin until a desired signal is obtained. Such gels are messy and preclude adhesion to the skin using conventional adhesives.

In view of the foregoing problems associated with ultrasound diagnosis, it would be advantageous to provide an ultrasound device which is structured to provide self-adherence of the device to the patient's skin thereby freeing the user's hands after positioning. It would further be advantageous to provide an ultrasound device which employs a coupling medium having inherent self-adherent properties and which provides consistent contact with the patient's skin to ensure proper transmission of the wave signal, and which reduces or eliminates the need for messy fluid-type gels.

SUMMARY OF THE INVENTION

In accordance with the present invention structure for providing self adherence of an externally-applied medical diagnostic device employs a skin-compatible, pressure sensitive, solid adhesive hydrogel as the contact medium between the diagnostic device and the patient's skin, and the invention is structured to adjustably adhere to the non-linear contour of a patient's body by means of a multi-positionable support element associated with the hydrogel. While the present invention is adaptable to a variety of medical diagnostic devices including without limitations those previously mentioned herein, this disclosure describes, by way of example only, use of the invention in fetal heart rate monitoring performed on a pregnant woman using an ultrasound transducer device.

Hydrogel films are polymeric or copolymeric materials which are relatively solid but have a high degree of flexibility and compliance. Gum-based adhesives may be added to give adhesive qualities when used, for example, as transdermal drug delivery patches. Further, because hydrogels may have inherent electrical conductivity, they are frequently used to fabricate electrodes for measuring the electrocardiogram. See, for example, U.S. Pat. No. 4,391,278 to Cahalan, et al., issued Jul. 5, 1983, and U.S. Pat. No. 4,593,053 to Jevne, et al., issued Jun. 3, 1986.

In the present invention, a hydrogel film is employed as the coupling medium between an ultrasound transducer and a patient's skin. Certain hydrogels have a density similar to body tissues and are therefore particularly acoustically suitable for use as a contact medium in ultrasound procedures. In addition, hydrogels used in the present invention are skin-compatible, pressure sensitive, solid and have inherent adhesive characteristics. The hydrogel of the present invention preferably comprises a layer of hydrogel material reinforced with a mesh substrate to produce a hydrogel film. Because film hydrogels are solids, they do not produce the mess that fluid gels do and they leave very little, if any, residue when removed from the skin. Film hydrogels are also non-irritative to the skin of most patients.

In the present invention, the hydrogel film is affixed to the under side of a medical diagnostic device, such as an ultrasound transducer device generally comprising a housing containing an emitter which produces the sound wave. Additionally, the ultrasound transducer may preferably include a receiver for receiving the emitted and reflected sound wave. The housing may have any shape or configuration, but a generally circular or disk-like configuration is particularly suitable.

The housing is generally adapted to receive a multi-positionable support element in association therewith. The support element is configured for attachment of at least a portion of the hydrogel film thereto. The support element keeps that portion of the hydrogel film which extends beyond the ultrasound housing from curling or bailing-up around the edges. Additionally, the support element provides multi-positioning of at least a portion of the hydrogel film against and away from the patient's skin and enhances adherence of the film to the patient's skin.

The multi-positionable support element includes, most suitably, a collar which encircles the ultrasound transducer housing. The support element is structured with means for providing flexibility of the support element proximate the housing to facilitate positioning of a peripheral portion of the support element from a first location proximate the patient's skin to a second location positioned away from the patient's skin. The hydrogel film is attached to the under side of the ultrasound transducer and to the multi-positionable support element so that the hydrogel film is located between the patient's skin and the ultrasound transducer structure with its associated support element.

The adjustability of the support element allows the ultrasound transducer to be moved about the patient's skin while the peripheral portion of the support element holds at least a portion of the hydrogel in a position away from the patient's skin. Once a meaningful signal is located, the support element periphery is flexed downwardly to assume a position proximate the patient's skin so that the adhesive hydrogel is held securely to the patient's skin. The peripheral portion of the support element, being flexible and therefore capable of assuming a plurality of positions, allows the hydrogel to gently contour the patient's body to enhance adhesion thereto. In the preferred embodiment of the invention, the downwardly-flexed support element periphery assumes a shallow cup-shaped configuration, which has proven to be extremely effective in maintaining the hydrogel film against the patient's skin without the presence of air pockets therebetween.

If repositioning of the transducer is required, the peripheral portion of the support element is flexed away from the patient's skin thereby positioning the associated portion of the hydrogel away from the patient's skin, and the ultrasound transducer is moved about the skin again until another signal is located. The support element is then flexed again to position the peripheral portion of hydrogel adjacent the patient's skin.

Because constant repositioning of the transducer during a lengthy ultrasound procedure may reduce the adhesive quality of the hydrogel, the support element allows the peripheral portion of hydrogel to be held away from the patient's skin during repositioning so that the adhesive quality of at least the peripheral portion of hydrogel is maintained. Lengthy ultrasound procedures may therefore be conducted without significantly compromising the effective adhesiveness of the peripheral hydrogel film. Further, due to the presence of the support element, the tendency of the peripheral portion of hydrogel to stick to itself during repositioning or to lose its effectiveness is eliminated.

Although the present invention is structured to conduct ultrasound procedures without use of traditional fluid-type coupling gels, such gels may be used in addition to the hydrogel film as required by the particular parameters of the procedure. Other types of lubricants may be used alternatively. Further, the adhesive qualities of hydrogels are generally enhanced by application of small amounts of water or other appropriate liquids to the hydrogel film surface, and the addition of such fluids may enhance the adhesive effect of the hydrogel film element against the patient's skin.

BRIEF DESCRIPTION OF THE ILLUSTRATED EMBODIMENTS

In the drawings, which illustrate what is currently considered to be the best mode for carrying out the invention, FIG. 1 is a view in cross section of the rounded abdomen of a pregnant women with a comparative, simplified ultrasound transducer positioned against the skin;

DETAILED DESCRIPTION OF THE ILLUSTRATED EMBODIMENT

Figure 1:
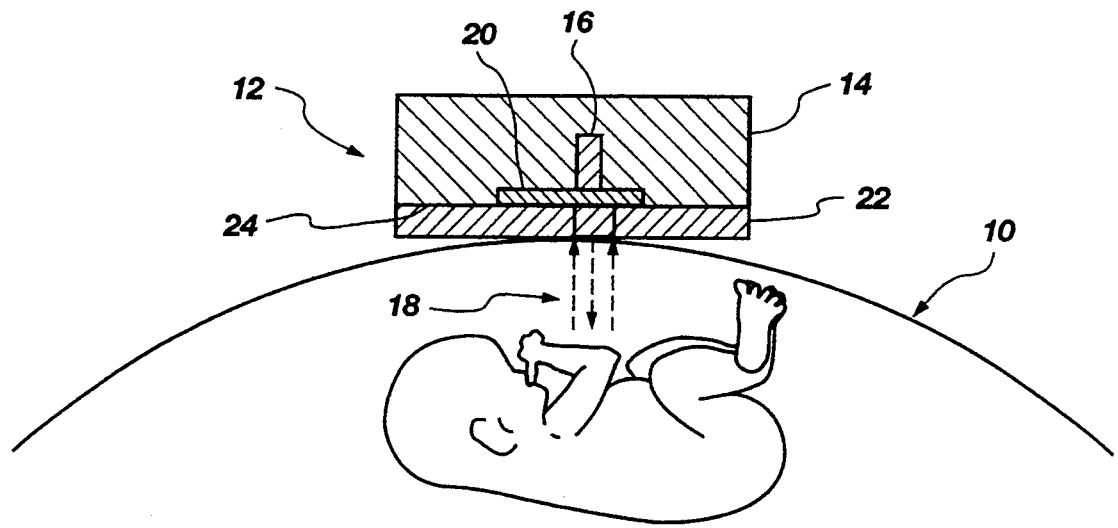

In FIG. 1, the rounded abdomen of a pregnant women is represented at 10, with a simplified ultrasound device 12 shown positioned against the patient's skin. The illustrated ultrasound device 12 of FIG. 1 is a generalized depiction of typical prior art ultrasound devices which comprise a housing 14 enclosing an emitter 16 for producing a sound wave, represented at 18, and a receiver 20 to detect the returning signal. Ultrasound devices, also termed transducers, in general may include structures in addition to those shown, but such structures have been omitted here for ease of illustration. Omission of ancillary structures for the ease of illustration of the invention is not intended to limit the scope of the invention.

A contact medium 22 is shown attached to the under side 24 of the prior art ultrasound device 12 in FIG. 1, positioned between the housing 14 and the patient's abdomen 10. The contact medium 22 here illustrated is a portion of hydrogel sized to cover the under side 24 of the housing 14 which does not extend beyond the outer perimeter dimensions of the housing 14. The housing 14 is generally circular in shape.

While a hydrogel contact medium 22 of the same footprint area as housing 14 provides certain advantages over the use of messy conventional fluid-type gels, it can be readily seen that the ultrasound device 12 is not stably maintained against the abdomen 10 of the patient because the specific nature of the hydrogel does not enable it to adhere a flat transducer base against the rounded abdomen of the patient. Thus, transducer 12 must be held in place by the user's hand or must be strapped to the patient. Additionally, in the illustrated configuration of FIG. 1, the peripheral edges of the hydrogel tend to curl inwardly and away from the under side 24 of the housing 14 thereby compromising the effectiveness of the contact medium.

Figure 2:
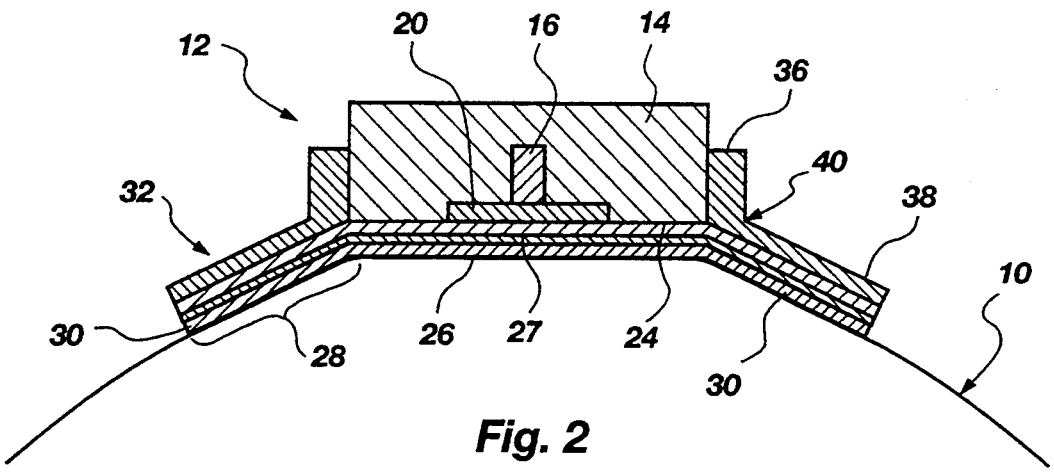
FIG. 2 is a view in cross section of the rounded abdomen of a pregnant women with an ultrasound transducer assembly of the present invention with support element in a downwardly-flexed position for adherence to the patient's abdomen.
Figure 3:
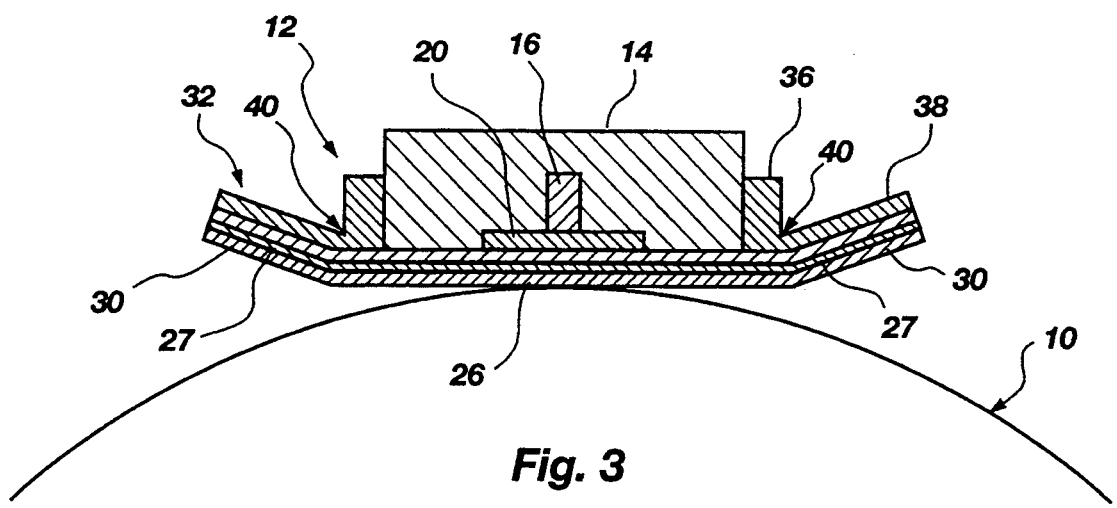
FIG. 3 is a view in cross section of the patient's abdomen shown in FIG. 2, showing the ultrasound transducer assembly of the present invention with support element in an upwardly-flexed position poised for movement about the patient's skin.
Figure 4:
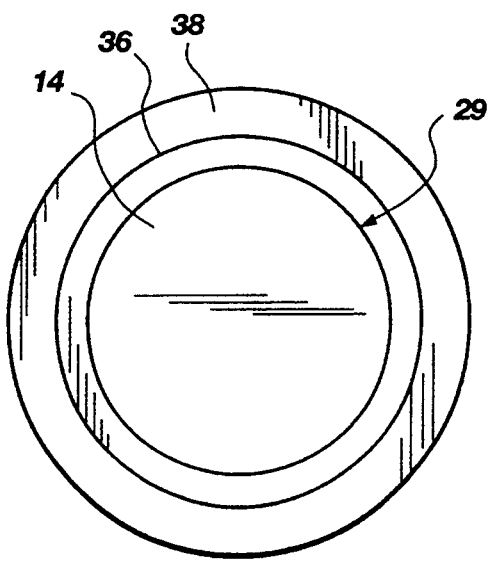
FIG. 4 is a plan view of the invention shown in FIG. 2.

The present invention, illustrated in FIGS. 2–4, is structured to overcome the problems previously described. Specifically, the present invention provides a hydrogel film 26 which attaches to the under side 24 of the ultrasound housing 14. The hydrogel 26 is a film formed by the association of hydrogel with a mesh substrate 27. The mesh substrate 27 maintains the hydrogel in a film and prevents stretching or tearing of the hydrogel material. Hydrogels which are hydrophilic, substantially solid, skin-compatible, pressure sensitive and adhesive are most suitable for use as a contact medium in the present invention. A particularly suitable hydrogel is Promeon ®, made by Promeon Company, a division of Medtronic, Inc., Minneapolis, Minn. Other suitable hydrogels are those manufactured by LecTec Corporation of Minnetonka, Minn.

The peripheral portion of the hydrogel 26 which extends beyond the perimeter 29 of the housing 14 forms a flap 30 having an inherent flexibility. The flap 30 of hydrogel film 26, which extends a selected distance 28 beyond the outer perimeter 29 (shown in FIG. 4) of the housing 14, facilitates adhesive securement of the transducer 12 against the skin of the patient without additional affixation means as required by prior art practices. The selected distance 28 to which the flap 30 extends past the perimeter 29 of the housing 14 is dictated by the amount of hydrogel film 26 needed to make the ultrasound transducer 12 self-adherent to the skin of the patient. A particularly suitable distance 28 of extension is approximately equal to twenty-five percent of the radius of the housing 14, if housing 14 and transducer 12 are circular in configuration.

Hydrogel films in an unsupported state have a tendency to self-adhere and the peripheral edges may curl inwardly. To address these problems, the present invention also includes a support element 32 to which the peripheral flap 30 of hydrogel 26 is attached. The support element 32 is associated with the housing 14 of the ultrasound device 12 and is endowed with sufficient flexibility and stiffness to maintain the flap 30 of hydrogel 26 apart from the patient's skin as described further hereinafter. The hydrogel 26 is attached to the support element 32 by virtue of its inherent adhesive quality. Promeon ®, for example, is manufactured with a release liner on both surfaces of the film. The first release liner is removed and the hydrogel film is positioned against the under side 24 of the housing 14 and against the associated support element 32. Then the second release liner is removed immediately before the ultrasound transducer 12 is to be applied to the patient's skin.

The support element 32 is structured to be flexibly movable proximate the point of connection of the support element 32 to the ultrasound housing 14. Consequently, the support element 32 provides multiple positioning of the flap 30 of hydrogel 26 which is attached thereto. This function is illustrated by FIG. 2 in which the support element 32 is flexed downwardly toward the patient's abdomen 10 in a shallow cup-shaped configuration to enhance adherence of the flap 30 of hydrogel 26 to the abdomen 10. The support element 32 may also be flexed upwardly away from the patient's abdomen 10, as shown by FIG. 3, to position the flap 30 of hydrogel 26 apart from the abdomen 10. Such flexibility of the support element periphery may be termed articulably rotational flexibility, as the outer edge of the support element periphery rotates upwardly and downwardly about a fixed inner edge of the periphery adjacent transducer 12.

In an exemplary ultrasound procedure, the ultrasound device 12, having the hydrogel 26 attached to the housing 14 and support element 32, and having the support element 32 flexed upwardly as shown in FIG. 3, is positioned against the patient's skin. The device 12 is repeatedly lifted from the skin and repositioned against the skin until a desired signal is located. Once a signal is located the periphery of support element 32 is then flexed downwardly, as shown in FIG. 2 to position the hydrogel 26, including flap 30, snugly against the patient's skin. Because the hydrogel 26 is inherently adhesive, it adheres to the patient's skin, aided in its adherence by the support element 32.

When it is desired to move the ultrasound device 12 or to locate a new signal, the support element 32 is flexed upwardly away from the skin and the device 12 is lifted. The device is repeatedly pressed against the skin and then removed therefrom until a desired signal is located. Once the signal is located the periphery of support element 32 is flexed downwardly again to adhere the hydrogel 26 to the skin to achieve self-adherence. Because repeated contact with and removal of the hydrogel 26 from the skin causes the hydrogel 26 to lose its adhesiveness, it can be seen that with the structure of the present invention, the adhesiveness of the flap 30 of hydrogel 26 is not compromised. Nonetheless, during a lengthy ultrasound procedure where the hydrogel is moved often, it may be necessary or desirable to moisten the hydrogel to rejuvenate its adhesiveness. Water may be used for this purpose. Additionally, fluid-type coupling gels may be used in small quantities to enhance mobility or adhesiveness of the hydrogel 26 during use. It should be noted that the cup-shaped configuration of support-element 32 in its downwardly-flexed position is particularly effective to produce a conforming and adhesive bond between the film of hydrogel 26 and the patient's skin.

Flexibility of the periphery of support element 32 may be achieved in a variety of ways. For example, as illustrated in FIGS. 2-4, the support element 32 may comprise a collar 36 which encircles the housing 14 of the ultrasound transducer 12. A skirt 38 of material is attached to or integrally formed with the collar 36 in a manner which provides flexible movement of the skirt 38 relative to the collar 36. Such flexibility may inherently reside with the material selected to form the collar 38 and/or skirt 38. For example, a synthetic rubber or other elastomeric material, or some type of resilient plastic, may provide sufficient flexion at the point of convergence 40 between the collar 36 and skirt 38 to facilitate movement of the skirt 38. Silicone rubbers, polyvinyl chloride and polyurethanes are contemplated as suitable materials for support element 32.

Figure 5:
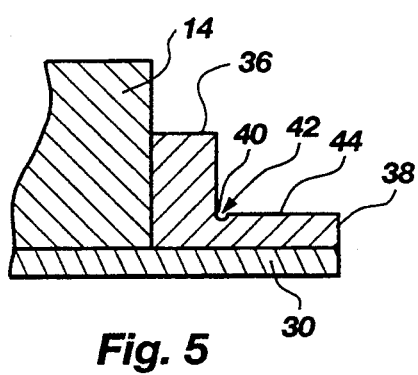
FIG. 5 is a view in cross section of a portion of the invention illustrating one means of enhancing flexibility of the support element periphery.
Figure 6:
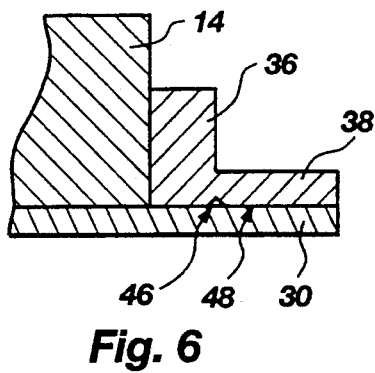
FIG. 6 is a view in cross section of a portion of the invention illustrating an alternative means of enhancing flexibility of the support element periphery.

Flexibility of movement between the skirt 38 and the collar 36 may be enhanced by structuring the skirt 38 with a groove 42 formed about the upper edge 44 of the skirt 38 at the point of convergence 40 between the collar 36 and skirt 38, as shown by FIG. 5. Alternatively, flexibility of the skirt 38 may be enhanced by structuring the skirt 38 with a notch 46 along the lower edge 48 of the skirt 38 at an approximate point of convergence between the collar 36 and the skirt 38, as shown by FIG. 6.

Figure 7:
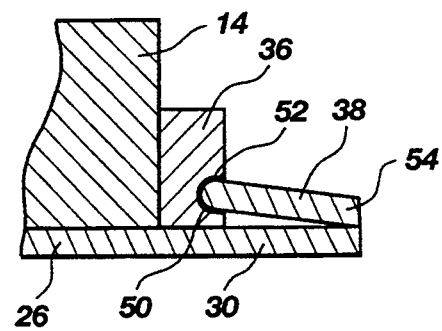
FIG. 7 is a view in cross section of a portion of the invention illustrating a second alternative means of enhancing flexibility of the support element periphery.

In another embodiment, illustrated by FIG. 7, skirt 38 may be attached to the collar 36 by insertion of a first, interior boundary 50 of the skirt 38 into a groove 52 formed in the collar 36 such that the skirt 38 is articulable with the collar 36. The second, exterior boundary and adjacent area 54 of the skirt 38 is attached to the flap 30 of the hydrogel 26 to provide movement thereto.

Figure 8:
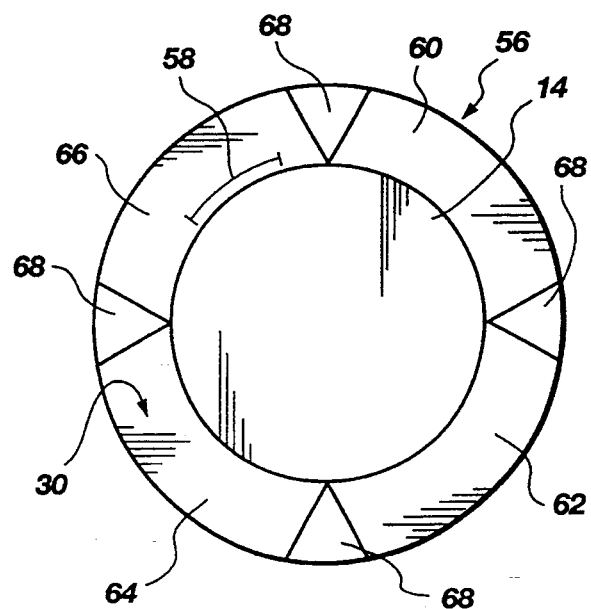
FIG. 8 is a plan view of an alternative embodiment of the support element of the invention.

In addition to the embodiments previously described, the support element 32 may merely comprise a skirt element 56 which is associated directly with the housing 14 of the ultrasound transducer 12, as illustrated by FIG. 8. The skirt element 56 may be an integral part of the housing where, for example, the housing may be molded or otherwise formed from a resilient plastic material which then extends outwardly to form the skirt element 56. In an embodiment where the skirt element 56 is integrated with the housing, the means illustrated in FIGS. 5 and 6 may also be employed to provide flexibility of the skirt element 56 relative to the housing. Alternatively, the skirt element 56 may not be integral with the housing 13, but merely associated therewith, and the means illustrated in FIG. 7, as well as other means, may be employed to provide flexibility to the skirt element 56.

In another embodiment, as pictorially represented by FIG. 8, the skirt element 56 may comprise a plurality of flaps 60, 62, 64, 66 of 24-mil polyester sheeting or other similar material, such as Mylar ®, extending beyond the perimeter 58 of the housing 14. Each flap 60, 62, 64, 66 is connected to the housing 14 and each is separated from another by a space 68. The flaps 60, 62, 64, 66 provide sufficient support to the hydrogel film 30, viewable through the transparent plastic, and facilitates moving the hydrogel film 30 from a first position adjacent the patient's skin to a second position away from the patient's skin. The plastic film, being slightly elastic, provides an amount of stretch to facilitate movement of the hydrogel to variable positions.

Figure 9:
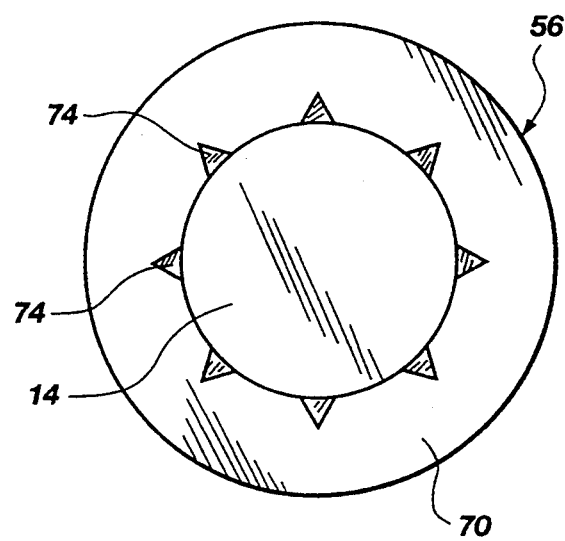
FIG. 9 is a plan view of a second alternative embodiment of the support element of the invention.

In yet another embodiment, as illustrated by FIG. 9, an integral film 70 of Mylar ® or similar material may form the skirt element 56. A plurality of notches 74 may be formed in the Mylar ® film 70 near the housing 14 to facilitate stretching of the skirt element 56 when being flexed between a first position adjacent the patient's skin to a second position spaced apart from the patient's skin. The skirt element 56 may engage a groove or notches on the periphery of housing, or may merely be forced over housing 14 and rest on a flange on the base of housing 14.

It should be noted that, while the housing 14 of the ultrasound device 12 is illustrated in the drawings as being circular, and the skirt 38 or skirt element 56 as circular to approximate the circular housing 14, the housing 14 of the ultrasound device 12 may in practice take any shape, size or configuration. The primary requirement for the invention is that the hydrogel film 26 extend a selected distance 28 beyond the housing 14, be sufficiently sized to provide securement of the device 12 to the patient's skin, and be supportable away from the patient's skin in such extended area 30 by a suitable support element.

The present invention is directed to a means of conducting ultrasound procedures in medical diagnoses, such as the aforementioned fetal monitoring, where the apparatus is self-adhering to the contour of the patient's body. The concept is also contemplated to be beneficial to many other applications involving patient monitoring, and the structure of the invention may be modified to meet the demands of each particular application. For example, audile monitoring of air flow through the heart during anesthesia may be enhanced through use of the present invention. Further, blood flow after surgery may be more readily auditorily monitored in areas beyond the surgical site. Hence, reference herein to specific details of the illustrated embodiments is by way of example only and not by way of limitation. It will be apparent to those skilled in the art that many additions, deletions and modifications to the illustrated embodiments of the invention may be made without departing from the spirit and scope of the invention as defined by the following claims.

What is claimed is:

1. Structure for providing adherence of an externally-applied medical diagnostic device to the skin of a patient comprising:

adhesive coupling medium having a central portion attachable to a diagnostic device configured with an external profile perimeter, said adhesive coupling medium being positionable between said device and the skin of a patient, said adhesive coupling medium being skin-compatible and pressure sensitive and sized with a flap portion which extends laterally a selected distance beyond said external profile perimeter of said diagnostic device; and flexible support structure attachable to said diagnostic device and substantially laterally coextensive with and attached to said flap portion of said adhesive coupling medium, said flexible support structure being configured to provide variable distance positioning of said flap portion relative to said skin of said patient and to selectively maintain said flap portion in a sustained position away from said skin when said central portion of said adhesive coupling medium is positioned against said skin.

2. The structure of claim 1 wherein said adhesive coupling medium is a film hydrogel having a first adhesive surface attached to said flexible support structure, and a second adhesive side positionable against said skin.

3. The structure of claim 2 wherein said hydrogel further comprises a mesh layer imbedded in said film.

4. The structure of claim 1 wherein said adhesive coupling medium is formed from a material having a density conducive to transmission of sound waves therethrough.

5. A transducer assembly for patient monitoring, comprising:

a housing containing an emitter for producing sound waves transmissible through the body tissues of said patient;

adhesive coupling medium positioned between said housing structure and the skin of said patient, said coupling medium having a density conducive to transmission of said sound waves through said body of said patient and being structured to provide self-adhesion of said assembly to said skin; and flexible support structure associated with said housing and attachable to said coupling medium to provide selectively sustained variable distance positioning of said coupling medium relative to and away from said skin of said patient.

6. The transducer assembly of claim 5 wherein said coupling medium is a film of solid hydrogel, said hydrogel being hydrophilic, skin-compatible and pressure sensitive.

7. The transducer assembly of claim 6 wherein said film of hydrogel extends beyond the perimeter of said housing a selected distance to provide enhanced adherence of said hydrogel to said skin.

8. The transducer assembly of claim 7 wherein said housing is round, and said selected distance is about twenty-five percent of the radius of said housing.

9. The transducer assembly of claim 7 wherein said flexible support structure extends beyond said perimeter of said housing to facilitate attachment of said extended hydrogel film thereto.

10. The transducer assembly of claim 9 wherein said flexible support structure comprises a skirt of material associated with said housing and shaped to substantially surround said perimeter thereof.

11. The transducer assembly of claim 10 wherein said skirt is notched in an area of said skirt proximate the housing to provide flexibility to said skirt when positioned at said variable distances away from said skin.

12. The transducer assembly of claim 10 wherein said skirt is articulable with respect to said housing.

13. The transducer assembly of claim 10 wherein said skirt comprises a plurality of flexible flaps extending outwardly from said housing, said flaps overlying said hydrogel film.

14. The transducer assembly of claim 10 wherein said support structure further includes a collar surrounding said perimeter of said housing and attached thereto, said skirt being attached to said collar.

15. The transducer assembly of claim 14 wherein said skirt is notched proximate the attachment of said skirt to said collar to provide flexibility to said skirt when positioned at said variable distances away from said skin.

16. The transducer as of claim 14 wherein said skirt is articulable with respect to said collar.

17. A transducer assembly for patient monitoring, comprising:

a housing containing structure to produce and detect sound waves transmissible through the body tissues of a patient, said housing having a perimeter;

adhesive contact medium having a central portion positioned between said housing and said skin of said patient to provide transmission of sound waves therethrough, said adhesive coupling medium being sized to extend laterally beyond said perimeter of said housing a selected distance, said contact medium having a selected density compatible with transmission of said sound waves through said body tissue; and flexible support structure associated with said housing and sized to extend laterally beyond said perimeter of said housing to support and retain said laterally extending adhesive coupling medium in at least one position away from said skin of said patient when said central portion of said adhesive coupling medium is positioned against said patient's skin.

18. The transducer assembly of claim 17 wherein said adhesive contact medium is a mesh-reinforced film of hydrogel, said hydrogel being hydrophilic, skin-compatible and pressure sensitive.

19. The transducer assembly of claim 18 wherein said flexible support structure is adjustable from a first position proximate said skin of said patient to a second position apart from said skin.

20. A method of performing ultrasound diagnoses comprising:

providing an ultrasound device having a housing containing structure for producing and detecting sound waves transmissible through the body tissue of a patient, an adhesive hydrogel film contact medium positioned between said housing and the skin of said patient to transmit sound waves therethrough, said hydrogel film being sized to extend beyond the perimeter of said housing, and flexible support structure associated with said housing to which said hydrogel film is secured, said flexible support structure providing adjustability of said extended hydrogel film relative to said skin;

adjusting said flexible support structure to position and retain said extended hydrogel film away from said skin;

placing said ultrasound device in proximity to said patient's skin with said hydrogel film positioned between said housing and said skin;

producing said sound waves from said ultrasound device;

moving said ultrasound device about said patient's body until a desired signal is detected by said ultrasound device; and adjusting said flexible support structure to position said extended hydrogel film against said skin to enhance adherence of said extended hydrogel film to said skin.

21. The method according to claim 20 further including:

repositioning said ultrasound device by adjusting said flexible support structure to position and retain said extended hydrogel film away from said skin;

moving said ultrasound device about said patient's skin until a desired new signal is detected; and adjusting said flexible support structure to position said extended hydrogel film against said skin.

22. The method according to claim 21 further including moistening said hydrogel before positioning said ultrasound device against said patient's skin prior to moving said ultrasound device about said patient's skin.

23. The method according to claim 22 wherein said hydrogel is moistened with a fluid-like coupling gel to enhance said adhesiveness of said hydrogel.

24. Structure for providing adherence of an externally-applied medical diagnostic device to the skin of a patient comprising:

a flexible support structure having an outer perimeter and an internal perimeter securable to an external profile of a diagnostic device, said outer perimeter of said flexible support structure being variably positionable relative to said internal perimeter, and said flexible support structure being configured to retain said outer perimeter of said flexible support structure in a first position on one side of a lateral plane formed through said internal perimeter and in a second position on an opposite side of said lateral plane formed through said internal perimeter; and adhesive coupling medium attached to said flexible support structure and being substantially coextensive therewith from said internal perimeter to said external perimeter thereof, said adhesive coupling medium having a central portion located within said internal perimeter of said flexible support structure and attachable to a diagnostic device, and said adhesive coupling medium further being substantially located within said lateral plane of said internal perimeter of said flexible support structure.

25. A self-adherent medical diagnostic device comprising:

support means having a central portion positionable against the skin of a patient, a peripheral outer edge and a laterally extending multipositionable skirt portion extending from proximate said central portion to said peripheral outer edge, said multipositionable skirt portion being rotationally deflectable with respect to the plane of said support means and self-retaining in at least two positions relative to said central portion; and an adhesive coupling medium attached to said support means for adherence of said support means to the skin of a patient, said adhesive coupling medium being substantially coextensive with said support means and being substantially continuous from any point proximate said peripheral edge and extending across said central portion to an opposite point proximate said peripheral outer edge.

26. The self-adherent medical device of claim 25 wherein said adhesive coupling medium further comprises means for permitting removal of said support means when adhered to a patient's skin and readherence of said support means to said skin at least one additional time.

27. The self-adherent medical device of claim 26 wherein said adhesive coupling medium is formed from a material having a density conducive to effective, substantially unimpeded transmission of sound waves therethrough.

28. The self-adherent medical device of claim 27 further including a housing attached to said support means, said housing containing a transducer oriented for generation of said sound waves through said adhesive coupling medium.

* * * * *